(12) United States Patent
Stahl

(10) Patent No.: US 6,637,197 B1
(45) Date of Patent: Oct. 28, 2003

(54) METHOD FOR CONTROLLING A RICH/LEAN COMBUSTION MIXTURE IN A DEFINED MANNER

(75) Inventor: Roland Stahl, Freiberg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/979,350
(22) PCT Filed: Apr. 29, 2000
(86) PCT No.: PCT/DE00/01378
§ 371 (c)(1), (2), (4) Date: Mar. 29, 2002
(87) PCT Pub. No.: WO00/71870
PCT Pub. Date: Nov. 30, 2000

(30) Foreign Application Priority Data

May 20, 1999 (DE) .......................... 199 23 044
May 19, 1999 (DE) .......................... 199 22 981

(51) Int. Cl.$^7$ .................................. F01N 3/00
(52) U.S. Cl. ................. 60/295; 60/274; 60/276; 60/285; 60/297
(58) Field of Search ............. 60/274, 276, 285, 60/295, 297, 301; 205/781, 782, 783

(56) References Cited

U.S. PATENT DOCUMENTS

| | | | |
|---|---|---|---|
| 5,643,429 A | * | 7/1997 | Wachman ............... 205/781 |
| 6,012,282 A | * | 1/2000 | Kato et al. .............. 60/274 |
| 6,378,295 B1 | * | 4/2002 | Heinze ................... 60/274 |
| 6,385,966 B2 | * | 5/2002 | Zhang .................... 60/274 |

FOREIGN PATENT DOCUMENTS

| | | | |
|---|---|---|---|
| DE | 196 36 790 | | 3/1998 |
| DE | 198 30 829 C1 | * | 4/1999 ........... 60/274 |
| EP | 0 678 740 | | 10/1995 |
| EP | 0 814 248 | | 12/1997 |

OTHER PUBLICATIONS

Kato N et al; "Performance of Thick Film NOX Sensor on Diesel and Gasoline Engines"; SAE Transactions, Journal of Engines, US, Warrendale, PA—1997; pp. 1246–1253.*

* cited by examiner

Primary Examiner—Thomas Denion
Assistant Examiner—Binh Tran
(74) Attorney, Agent, or Firm—Kenyon & Kenyon

(57) ABSTRACT

A method for selective rich/lean control of a combustion mixture using an electrochemical gas sensor. The method makes possible the operation of an $NO_x$ adsorption catalyst, which stores excess $NO_x$ present in the exhaust gas in a storage phase, the exhaustion of the storage capacity of the catalyst being expressed as an increase in the $NO_x$ concentration in the exhaust-gas stream after the catalytic converter, and which converts the stored $NO_x$ in a subsequent regeneration phase using a rich exhaust-gas mixture, the end of this reaction being able to be seen in a reduction in the lambda value of the exhaust-gas stream after the catalytic converter. The electrochemical gas sensor underlying the method for operating the $NO_x$ adsorption catalyst is operated such that the $NO_x$ and the oxygen concentrations in the exhaust-gas stream can be alternately determined using one and the same gas sensor.

12 Claims, 1 Drawing Sheet

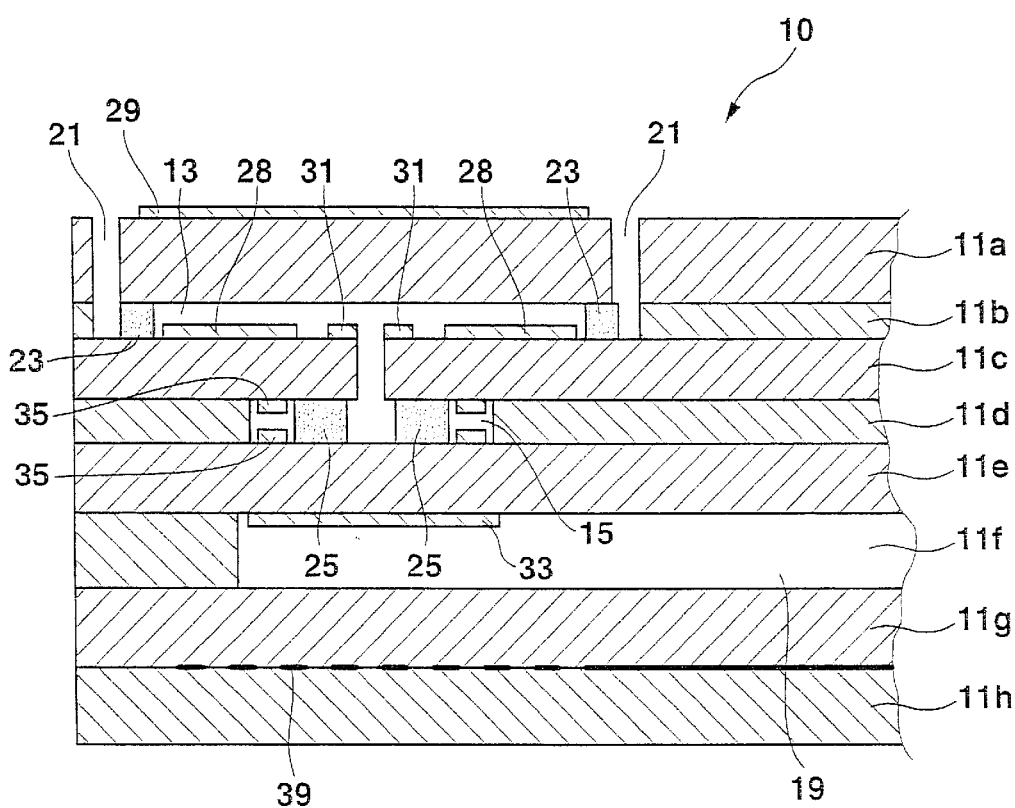

METHOD FOR CONTROLLING A RICH/LEAN COMBUSTION MIXTURE IN A DEFINED MANNER

The present invention relates to a method for selective rich/lean control of a combustion mixture using an electrochemical gas sensor according to the definition of the species in Claim 1.

BACKGROUND INFORMATION

In the course of fuel economy, internal combustion engines are preferably operated today using a lean combustion mixture. As a result, the nitrogen oxides $NO_x$ can no longer completely react in the catalytic exhaust-gas converter, since the necessary reducing components are no longer present in sufficient amounts. Because of this fact, so-called $NO_x$ adsorption catalysts are used that are capable of storing excess $NO_x$. However, this presupposes that the catalyst is regenerated from time to time, as soon as the storage capacity of the $NO_x$ adsorption catalyst is exhausted. For this purpose, the combustion mixture is set to be rich for a short time, until the stored $NO_x$ is completely converted and a new storage phase can be introduced. To be able to successfully carry out this rich/lean control, both a gas sensor for determining the $NO_x$, which detects the increase in the $NO_x$ concentration occurring at the end of the storage phase, and a gas sensor for determining the oxygen concentration, which analyzes the rich combustion exhaust with a particularly low oxygen content emerging from the catalytic converter at the end of the regeneration phase, are necessary in the exhaust-gas stream, in the flow direction, after the $NO_x$ adsorption catalyst.

An electrochemical gas sensor as described, for example, in Patent Application DE 199 12 102.8 can be used as the $NO_x$ gas sensor. It includes two chambers for the gas to be measured, each having a pump cell in different layer planes of a planar, oxygen ion-conducting, ceramic base material. Both pump cells include two electrodes deposited on a solid electrolyte. The gas to be measured flows via a first diffusion opening into the first measuring gas chamber where a first pump cell sets a constant low oxygen partial pressure by pumping oxygen in and out. With the aid of the electrical voltage (electromotive force) of a concentration cell (Nernst cell) also situated in the first measuring gas chamber, the oxygen partial pressure in the first measuring gas chamber is adjusted via the pump voltage of the pump cell. In a second measuring gas chamber, the $NO_x$ concentration in the measuring gas is determined in that the $NO_x$ contained in the measuring gas is decomposed on the surface of an electrode belonging to the second pump cell, and the oxygen resulting therefrom is pumped off together with the oxygen still remaining in the measuring gas.

An additional gas sensor, e.g. an oxygen sensor representing a lambda sensor, is needed to determine the oxygen concentration in the exhaust-gas stream. The disadvantage of this arrangement is the incorporation of two separate gas sensors, which entails an enormous cost disadvantage.

SUMMARY OF THE INVENTION

The method according to the present invention and having the characterizing features of Claim 1 has the advantage that a $NO_x$ gas sensor underlying the method, as described, for example, in Patent Application DE 199 12 102.8, is not only used to determine the $NO_x$ concentration in the measuring gas, but also to measure the oxygen concentration present there. This makes it unnecessary to install a separate oxygen sensor and makes possible the selective control of the combustion mixture using one and the same sensor.

According to one example embodiment of the present invention, a method for selective rich/lean control of a combustion mixture for an operation of an $NO_x$ adsorption catalyst, includes: storing $NO_x$ in a storage phase when the combustion mixture is set to be lean; converting the stored $NO_x$ in a regeneration phase when the combustion mixture is set to be rich; using an $NO_x$ concentration and an oxygen concentration in combustion exhaust gases in a flow direction behind the $NO_x$ adsorption catalyst for monitoring the storage phase and for monitoring the regeneration phase, respectively; determining the $NO_x$ concentration and the oxygen concentration by the same electrochemical gas sensor; and causing, using a measuring signal of the gas sensor, the storage phase to be initiated in response to a predetermined oxygen concentration not being attained, while a combustion mixture set to be rich is present.

The features set forth in the dependent claims make possible advantageous developments of the method recited in Claim 1. Furthermore, the dependent claims describe that, depending on the demand for precision of measurement, there is a plurality of different possibilities for operating the gas sensor for determining oxygen, and the method can, thus, be better adjusted to possible control engineering requirements.

BRIEF DESCRIPTION OF THE DRAWING

The present invention is explained in greater detail in the following description on the basis of a gas sensor represented in the drawing. The FIGURE shows a cross section of a gas sensor that can be used for implementing the method of the present invention.

EXEMPLARY EMBODIMENT

The FIGURE shows a principle design of a planar sensor element 10 of a gas sensor underlying the method. Sensor element 10 has, for example, a plurality of oxygen ion-conducting solid electrolyte layers 11$a$, 11$b$, 11$c$, 11$d$, 11$e$, 11$f$, 11$g$, and 11$h$. In this context, solid electrolyte layers 11$a$–11$h$ are designed as ceramic foils and form a planar ceramic body.

Sensor element 10 includes a first measuring gas chamber 13 and a second measuring gas chamber 15, which are superposed in different layer planes. Situated independently of the two measuring gas chambers 13, 15, in a further layer plane, for example, is a reference air channel 19, which is connected to the air atmosphere. Sensor element 10 further has two gas inlet openings 21, which direct the measuring gas into first measuring gas chamber 13. Formed at the entrances to first measuring gas chamber 13, in the diffusion direction of the measuring gas are first diffusion barriers 23, which are made, for example, of porous, ceramic material.

A further diffusion barrier 25 is formed in the diffusion direction of the measuring gas, between measuring gas chambers 13 and 15. Second measuring gas chamber 15 has, for example, an annular design, so that second diffusion barrier 25 also assumes an annular shape.

A first internal electrode 28 and a second internal electrode 31 are situated in first measuring gas chamber 13 Located on the outer large surface of solid electrolyte layer 11$a$ is a first external electrode 29, which is directly exposed to the exhaust gas. Located in second measuring chamber 15 is a third internal electrode 35, which, in the present example, consists of two mutually opposed, annular partial electrodes. A further external electrode 33, which is exposed to the air atmosphere, is located in reference air channel 19.

To be able to use sensor element 10 as an $NO_x$ sensor, third internal electrode 35, which is situated in measuring gas chamber 15, is made of a material that is capable of catalytically decomposing the $NO_x$. Such a material can be rhodium or a rhodium/platinum alloy. It is important that internal electrodes 28, 31, which are arranged upstream in the flow direction, essentially exhibit no catalytic activity with respect to the $NO_x$ decomposition. In this context, the electrode material for all electrodes is applied in a generally known way as cermet in order to sinter the electrode material to the ceramic foils.

Embedded in the ceramic base of sensor element 10, between two electrical insulating layers (not shown here) is a resistance heater 39. The resistance heater is used for heating up sensor element 10 to a necessary operating temperature.

Selective rich/lean control for operating the $NO_x$ adsorption catalyst.

If an internal combustion engine is operated using a lean combustion mixture, an excess of non-converted nitrogen oxides $NO_x$ is formed at the catalytic exhaust-gas converter. In the case of the $NO_x$ adsorption catalyst, they are stored temporarily and are first converted in a regeneration phase operated by a rich combustion mixture.

According to the present invention, above-described sensor element 10 is operated such that the gas sensor is arranged in the flow direction, downstream from the $NO_x$ adsorption catalyst and is operated as an $NO_x$ gas sensor during the lean phase. As soon as the storage capacity of the $NO_x$ adsorption catalyst is exhausted, this becomes noticeable as an increased concentration of $NO_x$ in the exhaust gas after the catalytic converter. This is detected by the gas sensor and results in the initiation of the regeneration phase using a rich combustion mixture. In this phase, a rich exhaust-gas mixture having a lambda value <1 is supplied to the $NO_x$ adsorption catalyst. However, due to the $NO_x$ reduction occurring in the adsorption catalyst, the exhaust gas exits the catalytic converter with a lambda value of approximately 1. As soon as the $NO_x$ stored in the adsorption catalyst is completely converted, the lambda value also falls in the exhaust gas after the catalytic converter. In the regeneration phase, the above-described gas sensor is operated as a lambda sensor that detects the lambda value decreasing after the $NO_x$ conversion is completed and causes the storage phase to be reintroduced.

A circuit configuration (not shown) is used to switch sensor element 10 from the operating mode as an $NO_x$ sensor to the operating mode as a lambda sensor and conversely. The electrodes of sensor element 10 are switched by the circuit configuration in accordance with the required operation mode.

Operating Mode as $NO_x$ Sensor

When using the $NO_x$ sensor, first external electrode 29 and first internal electrode 28 are operated as pump electrodes of a first pump cell. Second internal electrode 31 is connected to additional external electrode 33, which acts as a reference electrode, to form a concentration cell. Applied to electrodes 28, 29 is a pump voltage via which a constant oxygen partial pressure is set in first measuring gas chamber 13 by pumping oxygen in or out. In this context, the pump voltage applied to electrodes 28, 29 is regulated such that a constant voltage value is established at electrodes 31, 33 of the concentration cell.

The measuring atmosphere, which is set to a constant oxygen partial pressure, then reaches second measuring gas chamber 15 via diffusion barriers 25. Located in second measuring gas chamber 15 is a third internal electrode 35, which, in conjunction with reference electrode 33, is operated as a further pump cell. In this context, due to the catalytic material, third internal electrode 35 acts as an $NO_x$ sensitive electrode at which the $NO_x$ is decomposed according to the reaction $NO_x \rightarrow \frac{1}{2}N_2 + x/2\ O_2$. The pump current occurring in this context represents a measure for the sum of free oxygen and oxygen pumped off by the catalytic decomposition of $NO_x$.

Operating Mode as Oxygen Sensor

The design of sensor element 10 shown in the FIGURE can also be used as a so-called broadband sensor for determining the oxygen concentration. In the case of such sensors, this is performed by combining a pump cell with a concentration cell. The first pump cell including electrodes 28, 29 ensures the oxygen transport into or out of measuring gas chamber 13 of sensor element 10 to the extent that a predetermined potential is achieved at electrodes 31, 33 of the concentration cell. To set the predetermined potential, the pump current flowing between electrodes 28, 29 of the pump cell is used as a measuring signal proportional to the oxygen concentration.

A possible objection to this arrangement is that internal electrode 28 is designed such that it is catalytically inactive with respect to the $NO_x$ decomposition and does not permit any thermodynamic establishment of equilibrium of the measuring gas on the surface of the pump electrode. However, this would be necessary to precisely determine a lambda value. However, during the regeneration operation, the $NO_x$ can react with the rich gas components of the exhaust gas, such as CO, present in excess and is, thus, incorporated in the potential formation of the oxygen sensor. The operating mode as an oxygen sensor is, therefore, also precise with respect to $NO_x$.

The object of this invention is, however, not an exact determination of the lambda value, but the detection of a falling lambda value for reasons of control engineering.

A further specific embodiment including the underlying sensor element 10 is that electrodes 28, 29 do not necessarily have to be used as the pump cell, and electrodes 31, 33 do not have to be used for the concentration cell, but it is conceivable to use different combinations of the electrodes for the pump and concentration cells. Thus, in addition to the above-described first possibility, electrodes 31, 33 of the prevailing concentration cell can also be used as pump electrodes, and electrodes 33, 35 of the second pump cell can be connected to form the concentration cell.

A further advantageous specific embodiment including basic sensor element 10 is that first external electrode 29 and second external electrode 33 are operated as a Nernst cell, first external electrode 29 representing the exhaust-side electrode, and second external electrode 33 representing the reference air electrode of a conventional broadband sensor. During the regeneration operation, this sensor shows a voltage signal for lambda≅1 of 300–500 mV. The oxygen concentration, which decreases at the end of the regeneration operation, is detected as a potential jump from 300–500 mV to about 800 mV.

Not only a gas sensor having the described design of sensor element 10 is suitable for implementing the method of the present invention. Further embodiments of the sensor elements are also conceivable that enable the described operation mode as an $NO_x$ sensitive sensor or as a gas sensor for determining oxygen concentration.

What is claimed is:

1. A method for selective rich/lean control of a combustion mixture for an operation of an $NO_x$ adsorption catalyst, comprising:

storing $NO_x$ in a storage phase when the combustion mixture is set to be lean;

converting the stored $NO_x$ in a regeneration phase when the combustion mixture is set to be rich;

using an $NO_x$ concentration and an oxygen concentration in combustion exhaust gases in a flow direction behind the $NO_x$ adsorption catalyst for monitoring the storage phase and for monitoring the regeneration phase, respectively;

determining the $NO_x$ concentration and the oxygen concentration by the same electrochemical gas sensor; and causing, using a measuring signal of the gas sensor, the storage phase to be initiated in response to a predetermined oxygen concentration not being attained, while a combustion mixture set to be rich is present.

2. A method for selective rich/lean control of a combustion mixture for an operation of an $NO_x$ adsorption catalyst, comprising:

storing $NO_x$ in a storage phase when the combustion mixture is set to be lean;

converting the stored $NO_x$ in a regeneration phase when the combustion mixture is set to be rich;

using an $NO_x$ concentration and an oxygen concentration in combustion exhaust gases in a flow direction behind the $NO_x$ adsorption catalyst for monitoring the storage phase and for monitoring the regeneration phase, respectively;

determining the $NO_x$ concentration and the oxygen concentration by the same electrochemical gas sensor, the gas sensor including a first pump cell, a second pump cell and a concentration cell;

causing, using a measuring signal of the gas sensor, the storage phase to be initiated in response to a predetermined oxygen concentration not being attained, while a combustion mixture set to be rich is present;

setting a low oxygen partial pressure by an oxygen transport via the first pump cell to determine the $NO_x$ concentration contained in the combustion exhaust gases during the storage phase;

using the concentration cell for monitoring the oxygen concentration and using the second pump cell for transporting free oxygen and oxygen resulting from a decomposition of $NO_x$;

setting a low oxygen partial pressure by an oxygen transport via a pump cell to determine the oxygen concentration contained in the combustion exhaust gases; and using one of the first pump cell, the second pump cell and the concentration cell for monitoring the oxygen concentration.

3. The method according to claim 2, further comprising:

producing a low oxygen partial pressure during the regeneration phase by oxygen transport via the first pump cell, to determine the oxygen concentration; and using the concentration cell for monitoring the oxygen concentration.

4. The method according to claim 2, further comprising:

to determine the oxygen concentration, operating the second pump cell as a concentration cell during the regeneration phase and using the second pump cell for monitoring the oxygen concentration, while operating the concentration cell as a pump cell and producing a low oxygen partial pressure in the gas sensor by oxygen transport.

5. The method according to claim 2, further comprising:

connecting a first external electrode and a second external electrode to form a concentration cell functioning according to a potentiometric measuring principle; and using a potential difference occurring between the first and second external electrodes as a measuring signal for determining the oxygen concentration.

6. The method according to claim 2, further comprising:

causing, using the measuring signal of the gas sensor, the regeneration phase to be initiated when a predetermined $NO_x$ concentration is exceeded, while a combustion mixture set to be lean is present.

7. A method for selective rich/lean control of a combustion mixture for an operation of an $NO_x$ adsorption catalyst, comprising:

storing $NO_x$ in a storage phase when the combustion mixture is set to be lean;

converting the stored $NO_x$ in a regeneration phase when the combustion mixture is set to be rich;

using an $NO_x$ concentration for monitoring the storage phase;

using an oxygen concentration in combustion exhaust gases in a flow direction behind the $NO_x$ adsorption catalyst for monitoring the regeneration phase;

determining the $NO_x$ concentration and the oxygen concentration by the same electrochemical gas sensor; and causing, using a measuring signal of the gas sensor, the storage phase to be initiated in response to a predetermined oxygen concentration not being attained, while a combustion mixture set to be rich is present.

8. A method for selective rich/lean control of a combustion mixture for an operation of an $NO_x$ adsorption catalyst, comprising:

storing $NO_x$ in a storage phase when the combustion mixture is set to be lean;

converting the stored $NO_x$ in a regeneration phase when the combustion mixture is set to be rich;

using an $NO_x$ concentration for monitoring the storage phase;

using an oxygen concentration in combustion exhaust gases in a flow direction behind the $NO_x$ adsorption catalyst for monitoring the regeneration phase;

determining the $NO_x$ concentration and the oxygen concentration by the same electrochemical gas sensor, the gas sensor including a first pump cell, a second pump cell and a concentration cell;

causing, using a measuring signal of the gas sensor, the storage phase to be initiated in response to a predetermined oxygen concentration not being attained, while a combustion mixture set to be rich is present;

setting a low oxygen partial pressure by an oxygen transport via the first pump cell to determine the $NO_x$ concentration contained in the combustion exhaust gases during the storage phase;

using the concentration cell for monitoring the oxygen concentration and using the second pump cell for transporting free oxygen and oxygen resulting from a decomposition of $NO_x$;

setting a low oxygen partial pressure by an oxygen transport via a pump cell to determine the oxygen concentration contained in the combustion exhaust gases; and using one of the first pump cell, the second pump cell and the concentration cell for monitoring the oxygen concentration.

9. The method according to claim 8, further comprising:
producing a low oxygen partial pressure during the regeneration phase by oxygen transport via the first pump cell, to determine the oxygen concentration; and
using the concentration cell for monitoring the oxygen concentration.

10. The method according to claim 8, further comprising:
to determine the oxygen concentration, operating the second pump cell as a concentration cell during the regeneration phase and using the second pump cell for monitoring the oxygen concentration, while operating the concentration cell as a pump cell and producing a low oxygen partial pressure in the gas sensor by oxygen transport.

11. The method according to claim 8, further comprising:
connecting a first external electrode and a second external electrode to form a concentration cell functioning according to a potentiometric measuring principle; and
using a potential difference occurring between the first and second external electrodes as a measuring signal for determining the oxygen concentration.

12. The method according to claim 8, further comprising:
causing, using the measuring signal of the gas sensor, the regeneration phase to be initiated when a predetermined $NO_x$ concentration is exceeded, while a combustion mixture set to be lean is present.

* * * * *

UNITED STATES PATENT AND TRADEMARK OFFICE
CERTIFICATE OF CORRECTION

PATENT NO.        : 6,637,197 B1
APPLICATION NO.   : 09/979350
DATED             : October 28, 2003
INVENTOR(S)       : Roland Stahl It is certified that error appears in the above-identified patent and that said Letters Patent is hereby corrected as shown below:

Column 1, delete lines 5-8.

Column 1, line 34, change "in Patent Application DE" to --in German Patent Application No. DE--

Column 1, line 36, change "measured," to --measured (measuring gas chambers)--

Column 1, line 37, change "gas to be measured" to --gas to be measured (measuring gas)--

Column 1, delete lines 61-62.

Column 1, line 64, change "in Patent Application DE" to --in German Patent Application No. DE--

Column 2, delete lines 19-21.

Column 2, line 21, change "furthermore, the dependent claims described that," to --Furthermore,--

Column 2, delete lines 30-32.

Column 2, line 36, change "Exemplary Embodiment" to --DETAILED DESCRIPTION--

UNITED STATES PATENT AND TRADEMARK OFFICE
CERTIFICATE OF CORRECTION

| | |
|---|---|
| PATENT NO. | : 6,637,197 B1 |
| APPLICATION NO. | : 09/979350 |
| DATED | : October 28, 2003 |
| INVENTOR(S) | : Roland Stahl |

It is certified that error appears in the above-identified patent and that said Letters Patent is hereby corrected as shown below:

Column 3, lines 19-20, change "Selective rich/lean control for operating the $NO_x$ adsorption catalyst." to --Selective Rich/Lean Control for Operating the $NO_x$ Adsorption Catalyst--

Signed and Sealed this

Fifth Day of December, 2006

JON W. DUDAS
*Director of the United States Patent and Trademark Office*